(12) United States Patent
Fitremann et al.

(10) Patent No.: US 8,415,445 B2
(45) Date of Patent: Apr. 9, 2013

(54) FUNCTIONALIZED POLYSILOXANES, METHOD OF PREPARING SAME AND USES THEREOF

(75) Inventors: Juliette Fitremann, Toulouse (FR); Waêl Moukarzel, Toulouse (FR); Monique Mauzac, Toulouse (FR)

(73) Assignees: Centre National de la Recherche Scientifique (C.N.R.S.), Paris (FR); Universite Paul Sabatier Toulouse III, Toulouse (FR)

( * ) Notice: Subject to any disclaimer, the term of this patent is extended or adjusted under 35 U.S.C. 154(b) by 0 days.

(21) Appl. No.: 12/934,145

(22) PCT Filed: Mar. 24, 2009

(86) PCT No.: PCT/FR2009/050506
§ 371 (c)(1),
(2), (4) Date: Nov. 9, 2010

(87) PCT Pub. No.: WO2009/125126
PCT Pub. Date: Oct. 15, 2009

(65) Prior Publication Data
US 2011/0065863 A1    Mar. 17, 2011

(30) Foreign Application Priority Data

Mar. 25, 2008 (FR) ........................................ 0851895

(51) Int. Cl.
*C08G 77/12* (2006.01)
(52) U.S. Cl.
USPC .............................................. 528/31; 528/26

(58) Field of Classification Search ................. 528/31, 528/26
See application file for complete search history.

(56) References Cited

U.S. PATENT DOCUMENTS

| 6,686,342 B2 * | 2/2004 | Vournakis et al. ............ 514/55 |
| 2002/0082170 A1 | 6/2002 | Policello et al. |
| 2007/0128143 A1 | 6/2007 | Gruning et al. |
| 2008/0255305 A1 * | 10/2008 | Brook et al. ................ 525/103 |

FOREIGN PATENT DOCUMENTS

| DE | 19524816 A1 | 1/1997 |
| WO | 9429324 A1 | 12/1994 |
| WO | 02088456 A1 | 11/2002 |
| WO | 2005087843 A1 | 9/2005 |
| WO | 2005111116 A1 | 11/2005 |
| WO | 2006127924 A2 | 11/2006 |

OTHER PUBLICATIONS

DowCorning (Safe Handling of Silicon Hydride Containing Polysiloxanes, Aug. 2008).*
Freeman (Silicones, An Introduction to Their Chemistry and Applications, Published for the Plastics Institute, ILIFFE Books, Ltd. (1962)) (p. 27).*
International Search Report, dated Oct. 6, 2009, from corresponding PCT application.

* cited by examiner

*Primary Examiner* — Kuo-Liang Peng
(74) *Attorney, Agent, or Firm* — Young & Thompson

(57) ABSTRACT

Novel polysiloxanes grafted with at least one polyhydroxylated amino compound, method for preparing same and uses thereof.

20 Claims, No Drawings

FUNCTIONALIZED POLYSILOXANES, METHOD OF PREPARING SAME AND USES THEREOF

The object of the present invention is a polymer of the polysiloxane type comprising saccharide grafts. The object of the invention is also the method for preparing said polymers and the uses thereof.

Polysiloxanes are a class of polymers with many potential industrial applications. Nevertheless, they have hydrophobic properties which thereby limit their use. Giving them more hydrophilic properties was therefore considered for example by grafting groups of the polyethylene oxide, pyrrolidone type or further with charged groups of the quarternary ammonium type. These polysiloxanes are used within the scope of various formulations of the emulsion type or for modifying the wetting of surfaces, such as lubrication or anti-fog treatments. On the other hand, they may find applications with more difficulty in the biological and medical fields because of their much less favorable toxicological profile. Saccharide grafts were therefore contemplated for extending the field of application of polysiloxanes, notably for biomedical applications. These "glycopolysiloxanes" are particularly interesting in that they combine the unique mechanical properties of polysiloxanes with hydrophilicity and biocompatibility properties of saccharide groups.

Different strategies for grafting sugars on polymers of any kinds have been elaborated. Certain of them allow direct grafting of saccharide groups without any protective groups and therefore include less steps, but are limited by selectivity problems of the coupling reaction (because of the multiple hydroxyls borne by the saccharides). Only certain types of saccharide groups allow the coupling to be achieved selectively without resorting to protective groups. Other strategies resort to protective groups, in order to have a single site for grafting the saccharide group, but include multiple steps, incompatible with technological development. In the case of one-dimensional polymers, selectivity is a crucial point, since the introduction of a non-selective graft which may react through several of its functions, leads to an undesired crosslinked material.

These different strategies for making "glycopolymers" were able to be described for different types of polymer backbones, other than polysiloxanes, e.g. for polymethacrylates. However, their transposition to one-dimensional polysiloxanes proves to be impossible or difficult to achieve due to the specificity of the Si—O bond. The latter is indeed very fragile, notably in the presence of a base or an acid, and notably in the case of polysiloxanes in solution. Thus, alternative methods have to be developed in order to preserve the integrity of the polysiloxane chain during the grafting. Among the described methods, very few of them allow this integrity to be retained.

As regards the strategies not using protective groups, the most standard method consists of grafting a sugar lactone on an amino polysiloxane as notably described in documents WO 2002/088456, WO 2006/127924, Stadler et al., *Makromol.* 28, 1, 1995, 17-24. Nevertheless, this strategy is very limited insofar that the amino polysiloxanes are accessible with difficulty, the length of the polymer being less than about 7,000 g/mol and functionalization levels being low generally less than 10%.

An alternative consists of forming an intermediate of the polymer by hydrosilylation with an epoxy derivative, of having it react with a diamine and then grafting a sugar lactone on the free-remaining amine. Nevertheless, the reaction is long and requires heating which may lead to a partial degradation of the polymer (Wagner et al., *Appl. Organomet. Chem.* 1996, 10, 421-435). It may also lead to a crosslinked material because of the bi-functionality of the amine.

Thiem et al., *Polymer*, 2004, 7053-7059 propose an original approach to the synthesis of sugar copolymers and of polysiloxanes in which sugar units are however included into the chain.

FR 2 900 931 proposes a "click chemistry" method (by 1,3-dipolar cycloaddition catalyzed by Cu(I)), wherein the polysiloxane and the saccharide are connected through a group comprising a triazole structure. However, this method requires one to two additional steps for preparing allylated sugars, not available commercially, as well as the heating of the polysiloxane in the presence of an acid.

Application WO 2005/111116 describes the grafting of surfaces of silicone elastomers with activated esters. These activated esters may then react with any type of biomolecules. The grafting of heparin is described. Nevertheless, the crosslinked elastomers of silicones do not have the same fragility as non-crosslinked polysiloxanes. Also, because of the presence of multiple amine groups in heparin, the latter would cause the formation of multiple bonds with the polysiloxanes and would therefore lead to crosslinked and poorly defined material.

The other methods, for example described by Hamaide et al. (*Macromolecular Chem. Phys.* 2005, 206, 1757-1768) or WO 2005/087843, describe methods comprising functionalization of saccharides with a terminal alkene group, production of available hydroxy groups, hydrosilylation allowing the grafting of the protective saccharide onto the polysiloxane, and finally, deprotection. However, these methods are long and may lead to degradation of the Si—O bonds during the step for deprotecting the saccharides.

Each of the methods described above remains unsatisfactory in that they require a long and/or costly large-scale synthesis strategy, limited starting products or difficult to access and/or final products with a very specific structure, and/or lacking selectivity and/or leading to more or less significant degradation of the polysiloxane. It is therefore desirable to make available a simple synthesis route, starting with current and/or easily accessible polysiloxanes.

Thus, the present invention proposes polysiloxanes grafted with at least one monoaminated saccharide, said monoaminated saccharide(s) being bound by the nitrogen atom of said amino group to a —C=O— group of said polysiloxane so as to form a —C(=O)—NT- group, wherein T represents a hydrogen atom or an alkyl or aryl group.

Said grafted polysiloxanes according to the invention are designated hereafter as glycopolysiloxanes.

More specifically, said grafted polysiloxanes fit either one of the following general formulas:

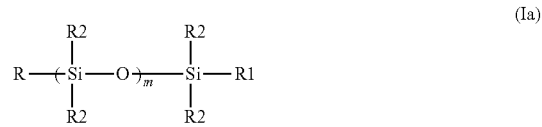

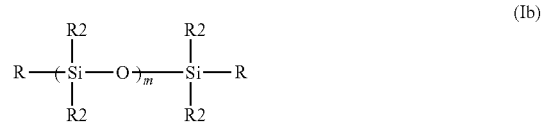

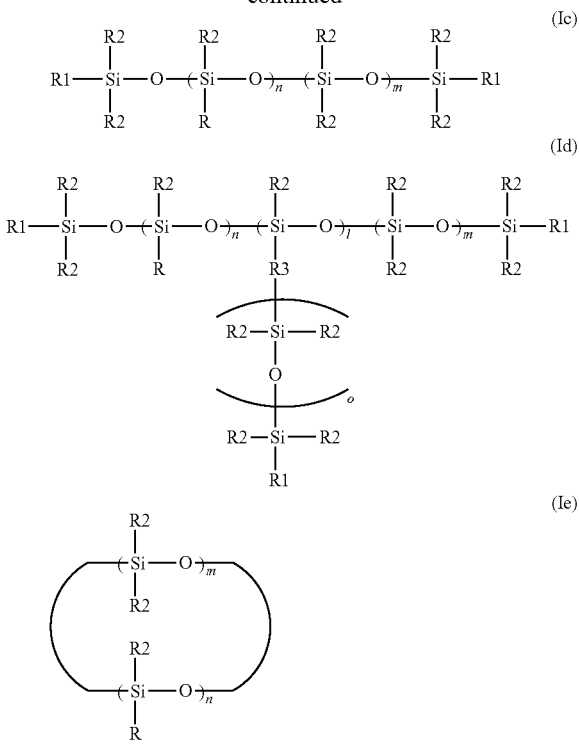

wherein:
each of R1, R2, either identical or different, is a hydrogen atom or a saturated, unsaturated or aromatic, linear, branched or cyclic, hydrocarbon group optionally comprising one or more heteroatoms, such as O, S or N, and/or one or more halogen atoms and/or epoxide, acrylic groups, C=O, COOU, COU, cyano, NUV, CONUV groups wherein U and V, either identical or different, represent independently a hydrogen atom or an alkyl group;
each of the identical or different R groups, is a group of formula —X—C(=O)—NT-Y; wherein
X represents an aryl, alkyl, perfluoroalkyl group, with 4 to 22 carbon atoms, optionally comprising one or more oxygen atoms so as to form for example a chain of the PEG type;
T represents a hydrogen atom or an alkyl or aryl group;
Y represents a remainder of a saccharide group such that Y-NTH represents said monoaminated saccharide;
R3 represents a crosslinking bridge, such as a saturated, unsaturated, or aromatic, linear, branched or cyclic hydrocarbon group, optionally comprising one or more heteroatoms such as O, S or N, and/or one or more halogen atoms and/or epoxide, acrylic groups, C=O, COOU, COU, cyano, NUV, CONUV groups wherein U and V, either identical or different, represent independently a hydrogen atom or an alkyl group; notably benzophenone;
n represents an average number strictly greater than 0;
m, l and o, either identical or different, represent average numbers greater than or equal to 0,
such that the grafting ratio n/(m+n) or n/(l+m+n+o) is comprised between 1/1,000 and 1;
it being understood that in the formulae (Ia), (Ib), (Ic), (Id) and (Ie) represented above, the polysiloxanes may be grafted with one or more saccharide groups randomly or blockwise.
Preferably, each of R1 and R2, either identical or different, represents an alkyl, aryl or polyether group such as polyethylene glycol (PEG).
Preferentially, m+n or l+m+n+o is less than 10,000.
The term "polysiloxane" used here refers to polymers of the silicone type. The polysiloxane backbones according to the invention may be selected from any marketed polysiloxane or prepared according to methods known per se.
Preferably, X represents an alkyl chain of 4 to 22 carbon atoms, optionally comprising one or more oxygen atoms so as to form e.g. a chain of the PEG type, more preferentially an alkyl chain.
The expression "remainder of a saccharide group" refers to the remainder of the monoaminated saccharide resulting from the grafting, it being understood that said monoaminated saccharide is grafted via said nitrogen atom.
The expression of "monoaminated saccharide" refers to saccharides and/or derivatives of saccharides, comprising one amine group. Said amine may be primary or secondary.
By "saccharide", is meant any molecule comprising at least one saccharide unit, such as monosaccharides, as well as oligosaccharides and polysaccharides.
By "derivatives of saccharides", are notably meant their reduced derivatives such as alditols or polyols or their oxidized derivatives such as aldonic acids, uronic acids.
As examples of monosaccharides or of their derivatives, mention may be made of: glucose, fructose, sorbose, mannose, galactose, talose, allose, gulose, idose, rhamnose, arabinose, xylose, lyxose, ribose, fucose, gluconic acid, glucuronic acid, galacturonic acid.
As examples of di- or oligo-saccharides, mention may be made of: maltose, gentiobiose, lactose, cellobiose, isomaltose, melibiose, saccharose, palatinose, isomaltose, leucrose, laminaribiose, xylobiose, mannobiose, sophorose, cellotriose, panose, maltotriose, isomaltotriose, maltotetraose, maltopentaose, maltohexaose maltoheptaose, mannotriose, fructooligosaccharides, glucooligosaccharides, inulin.
As examples of polysaccharides, mention may also be made of starch and of its derivatives, maltodextrins, galactomannans and their derivatives, for example guar polymers and their derivatives, obtained by hydrolysis of natural guar, cellulose, dextrans, amylopectin, xyloglucans, levans, and optionally their chemical modification (derivatization).
Monoaminated saccharides according to the invention therefore include the monoaminated analogs of the compounds above as well as their derivatives. As monoaminated saccharides according to the invention, mention may notably be made of: aminoalditols, notably glucamine, N-methyl-glucamine, galactamine, N-methyl-galactamine, mannamine, N-methyl-mannamine, aminosugars such as glucosamine, galactosamine, mannosamine, fucosamine, allosamine, altrosamine, ribosamine, arabinosamine, gulosamine, idosamine, talosamine, xylosamine, lyxosamine, sorbosamine, tagatosamine, psicosamine and fructosamine, or their derivatives, or further glycosylamines such as glucosylamine, galactosylamine, mannosylamine, fucosylamine, xylosylamine, arabinosylamine, ribosylamine, fructosylamine, sorbosylamine, talosylamine, allosylamine, gulosylamine, idosylamine, rhamnosylamine, lyxosylamine, and the other glycosylamines obtained by monoamination in an anomeric position of other monosaccharides, as well as of reducing disaccharides, oligosaccharides or polysaccharides, such as maltose, gentobiose, lactose, cellobiose, isomaltose, melibiose, saccharose, palatinose, isomaltose, leucrose, laminaribiose, xylobiose, mannobiose, sophorose, cellotriose, panose, maltotriose, isomaltotriose, maltotetraose, maltopentaose, maltohexaose, maltoheptaose, mannotriose, fructo-oligosaccharides, gluco-oligosaccharides, inulin, starch, dextrans, cellulose. This definition also includes monoaminated derivatives of saccharides which may be prepared by grafting an amine function on saccharides as defined earlier. For example, those which may be obtained by addition of a diamine on a sugar lactone, such as gluconolactone, lactonolactone, galactonolactone, mannonolactone, or disaccharides, oligosaccharides, polysaccharides such as those mentioned earlier and terminated by a sugar lactone, or other sugar lactones derived from the oxidation of mono-, di-, oligo- or poly-saccharides.

Glucamine, N-methylglucamine, glucosamine, galactosamine, mannosamine, glycosylamines or any saccharide substituted with an amine group and more particularly glucamine, notably D-glucamine are notably preferred.

By alkyl are meant branched or linear hydrocarbon groups comprising, unless particularly mentioned, from 1 to 20 carbon atoms, preferentially from 1 to 6 carbon atoms.

By aryl are meant mono- or bi-cyclic aromatic hydrocarbon groups with 5 to 10 carbon atoms, such as phenyl or naphthyl.

According to another object, the present invention also relates to the method for preparing glycopolysiloxanes according to the invention.

Said method comprises the step for coupling a grafted polyxiloxane with an activated ester, with a monoaminated saccharide according to the invention.

Said polysiloxane grafted by an activated ester fits one of the general formulae (IIa)-(IIe):

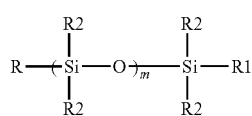
(IIa)

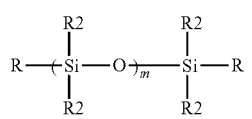
(IIb)

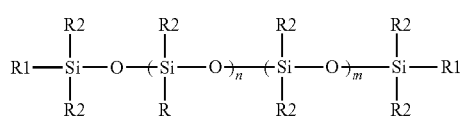
(IIc)

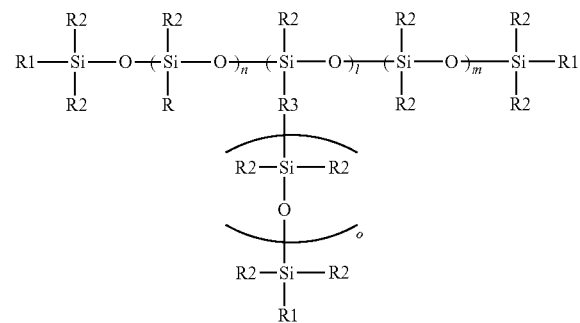
(IId)

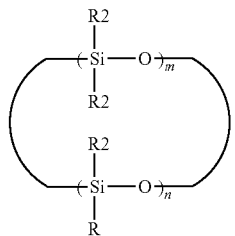
(IIe)

wherein:
R1, R2, R3, n, m, l, o are as defined in general formula (Ia)-(Ie) and
each of the R groups, either identical or different, is a group of formula —X—C(=O)-A wherein
X is defined as in general formulae (Ia)-(Ie) and A represents an activator group of the carboxylic acid function.

In a preferential embodiment of the invention, the monoaminated saccharides are available in their basic form (free amine), and do not include any other residual base. If they are not directly available in this basic form, but in their acid form (ammonium), non-reactive towards activated esters, they are transformed in their basic form and are advantageously purified from any other base having been used for this transformation, by a suitable purification method known per se, before their reaction with polysiloxane. Indeed, it was observed that the presence of any residual base may cause degradation of the polymer and should therefore be avoided. Advantageously, the coupling reaction is therefore achieved without providing any additional base. When the basic form of the monoaminated saccharide was prepared by adding a base, the base residues were reduced to a minimum, preferentially less than 10% of the monoaminated saccharide.

In a preferential embodiment of the invention, the grafting of the polysiloxane including the activated esters is achieved with D-glucamine.

The group A may be selected from any carboxylic acid function activator group customarily used. Mention may notably be made of the groups of type:
  O-succinimide wherein the succinimide group may optionally be substituted, for example with a sodium sulfonate group, or optionally fused with a phenyl group;
  S-alkyl or S-aryl or S-pyridyl wherein the alkyl, aryl or pyridyl groups are optionally substituted with halogen atoms, such as fluorine;
  —O-para-nitrophenyl and its derivatives;
  O-pentafluorophenyl;
  O-pentachlorophenyl;
  O-benzotriazole and its derivatives;
  O-benzotriazine and its derivatives;
  2,2,2-trifluoroethyl;
  N-imidazole and its derivatives.

This reaction may be carried out in a suitable solvent for example DMF or DMSO with which the two reagents may be miscibilized together. Unexpectedly, it was observed that the grafted one-dimensional polysiloxanes grafted with activated esters become soluble in polar solvents, such as DMF or DMSO, which has a great advantage for the reaction with the saccharides. Indeed, a drawback very often encountered in the methods described earlier consists in the impossibility of finding a solvent capable of miscibilizing both the siloxane and the non-protected saccharide, leading to poor reactions.

The selection of the solvent may nevertheless be adapted to the value of n/n+m+l. The solvent will be selected from tetrahydrofurane, dioxane, acetonitrile, DMF, DMSO, water or mixtures of these solvents, depending on the value of n/n+m+l. A solvent or a mixture of less polar solvents will be preferred for smaller values of n/n+m+l and a solvent or a mixture of more polar solvents for the strongest values of n/n+m+l. The reaction may be conducted at a temperature comprised between −50° C. and 100° C., preferably at room temperature. The reaction occurs advantageously in a homogeneous phase and without adding any base. Also advantageously in comparison with the other methods, the reaction is quasi-instantaneous at room temperature, and therefore does not require any prolonged heating.

Generally, the grafting level is not limited and exclusively depends on the nature of the starting polysiloxane.

The polysiloxane grafted by an activated ester may be prepared by any means, notably by applying or adapting the procedure described by Ringsdorf et al., *Angew. Chem. Int. Ed. Engl.*, 26 (1987), 11, 1178-1180. More specifically, the polysiloxane grafted with an activated ester may be made by hydrosilylation of the starting polysiloxane comprising at least one SiH group, of the corresponding formulae (IVa)-(IVe):

(IVa)

(IVb)

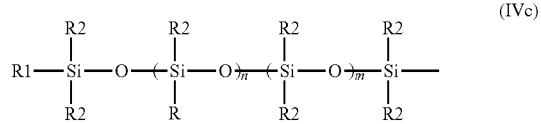
(IVc)

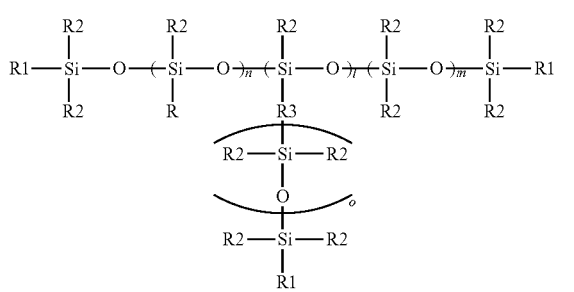
(IVd)

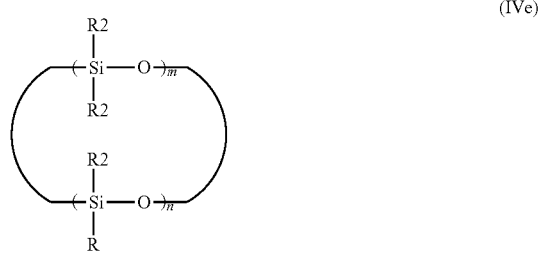
(IVe)

wherein R1, R2, R3 are as defined hereinbefore, and R represents a hydrogen atom, with an activated ester of formula (III):

$$CHR'=CR''—Z—C(=O)-A \qquad (III)$$

wherein:

R' and R'', either identical or different, represent independently a hydrogen atom or an alkyl group, Z represents an alkyl, aryl, perfluoroalkyl group, with 2 to 20 carbon atoms, optionally comprising one or more oxygen atoms so as to form for example a chain of the PEG type, and A represents an activator group of the carboxylic acid function, as defined earlier, It being understood that —CHR'—CHR''—Z— is equal to X, in the presence of a suitable catalyst, for example a platinum catalyst.

As a suitable catalyst, mention may notably be made of $Pt(Et_2S)_2Cl_2$, $Pt((PhenylCH_2)_2S)_2Cl_2$, dicyclopentadienylPtCl$_2$, $H_2PtCl_6$, Karstedt's catalyst (platinum/divinyltetramethyldisiloxane complex), $PtO_2$; $Pt(Et_2S)_2Cl_2$, $Pt((PhenylCH_2)_2S)_2Cl_2$ and Karstedt catalyst are most particularly preferred.

The amount of catalyst to be used depends on the catalyst, on the reaction to be carried out and on the experimental conditions. Generally, less than 5% of catalyst is used, preferentially between 0.01 and 1% based on the amount of Si—H functions. The solvent of this reaction may be selected from suitable solvents with which the activated ester may be solubilized, such as THF, toluene. Advantageously, the reaction occurs at a temperature comprised between room temperature and the reflux temperature of the solvent, for example between 50 and 90° C.

As an activated ester, the hydroxysuccinimide ester of undec-10-enoic acid, that of pent-4-enoic acid, that of [2(2-propenyloxy)ethoxy]acetic acid are preferred.

The activated ester may available commercially or may be prepared by applying or adapting a method known per se. For example, the activated ester may be prepared by direct esterification of N-hydroxysuccinimide with the acid, $CH_2=CR'—Z—C(=O)—OH$, according to the method described by Hassner et al., *Tetrahedron Lett* 46 (1978), 4475.

The hydrosilylation reaction with the activated ester and the coupling reaction with the amino saccharide may advantageously be carried out successively in "a single pot", without any intermediate purification.

In order to prepare the compound of formula (Id), it is also possible to operate by crosslinking of the corresponding compounds (Ic) wherein m is different from 0, by applying methods known per se.

The starting polysiloxanes comprising at least one SiH group are available commercially, marketed for example by Gelest or may be prepared according to methods known per se.

The preparation method also comprises the optional subsequent step consisting of purifying or isolating the desired grafted product. Advantageously, this purification may be carried out by washing with water.

The glycopolysiloxanes according to the present invention may be useful in all the fields of application of polysiloxanes, and more particularly when more hydrophilic properties of said polysiloxanes are desirable.

Thus, they may notably be used as a surfactant and more particularly as a surface agent, emulsifier, co-emulsifier, dispersant, co-dispersant, adhesive or component of an adhesive, notably in pharmaceutical or cosmetic compositions.

They may also be used in inplants, as biomaterials or additives of biomaterials, as a support for cell cultures for tissue engineering or as vectorization agents for active ingredients. The glycopolysiloxanes according to the invention may also find uses in micro- and nano-systems, notably in micro- or nano-fluidics, in order to be deposited on a silicon, glass support or any other support.

The following examples are given as an illustration and not as a limitation of the present invention.

EXAMPLE 1

Preparation of poly-(N-glucamine-undecylamide-methyl-co-dimethyl)-siloxane containing 40% of Si—N-glucamine-undecylamide. ($MD_x^{Glu}D_yM$ (x=0.4 and y=0.6))

Preparation 1

Synthesis of the starting polysiloxane, poly(hydromethyl-co-dimethyl)siloxane $MD_x^HD_yM$ The operating procedure is the following (for a copolymer containing 40% of —SiH(CH$_3$)—O— units) i.e. x=0.4 and Y=0.6):

In a reactor provided with a magnetic stirrer, 125 mg of catalytic resin Spherosil® (sulfonated crosslinked divinylbenzene resin (Spherosil® [H$^+$]=0.5 meq/g provided by Rhône Poulenc—Thesis of N. Leroux University of Bordeaux I (1993)) (the catalyst proportion in the reaction medium is 1.1 g for 100 g of mixture) are introduced beforehand under an inert atmosphere. They are heated for one hour to 60° before introducing 100 mmol of D$_4$ (octamethylcyclotetrasiloxane) i.e. a mass of 7.4 g, and 67 mmol of $MD^HM$ (polyhydromethylsiloxane) i.e. a mass of 4.1 g. Heating is performed for 3 days at 60° C. with gentle stirring. The mixture diluted in toluene in the presence of decalite (diatoms) is filtered on a filtration cone of 0.2 µm in order to remove any trace of catalyst. Evaporation in vacuo is performed for several hours in order to remove the small chains.

This step may also be carried out by means of the following catalyst:
Tonsil Optimum 214 FF provided by Süd-Chemie (G. Sauvet et al., *Journal of polymer Science*: Part A: Polymer Chemistry 38, 826 (2000)) used with a proportion from 0.5 to 2% by mass relatively to the reaction medium).
Characterization
SEC DPn 100 (Elution volume in toluene=21 mL)
FTIR: 2964 cm$^{-1}$ (CH$_3$) 2160 cm$^{-1}$ (Si—H) 1261 cm$^{-1}$ (Si—CH$_3$) 1000-1100 cm$^{-1}$ (Si—O—Si)
$^1$H NMR (300 MHz, CDCl$_3$): (δ ppm) 0.2 (Si—CH$_3$) 4.7 (Si—H)
$^{13}$C NMR (100 MHz, CDCl$_3$): (δ ppm) 1.0 (Si—CH$_3$)
$^{29}$Si NMR (79.5 MHz, CDCl$_3$): (δ ppm) −20.5 (tm, D); −36.5 (tm, D$^H$)

Preparation 2

Synthesis of the Activated Ester, Succinimidyl Undecenoate

A mixture of undecenoic acid (1 g (5.42 mmol)), of N-hydroxysuccinimide (0.68 g (5.9 mmol)) and dicyclohexylcarbodiimide (1.22 g (5.9 mmol)) is dissolved in 50 mL of THF at 0° C. for 10 minutes. The mixture is left at room temperature for 48 hrs. The white precipitate formed on a filtration cone (sintered glass) is removed and the solvent is evaporated under reduced pressure. The residue is purified by recrystallization from hexane.
Characterization:
$^1$H NMR (300 MHz, CDCl$_3$): (δ ppm) δ 0.8 (m, 3H); δ 1.2 (m, 10H); δ 1.6 (m, 2H); δ 1.95 (m, 2H); δ 2.5 (t, 2H); δ 2.74 (s, 4H); δ 4.8 (m, 2H); δ 5.7 (m, 2H)
$^{13}$C NMR (100 MHz, CDCl$_3$): (δ ppm) δ 24.3, 25.5, 28.7, 28.8, 28.9, 29.1, 30.8, 33.7, 139.1, 168.7, 169.3.

Preparation 3

Grafting of the poly(hydromethyl-co-dimethyl)siloxane copolymer (Preparation 1) with the activated ester succinimidyl undecenoate (Preparation 2): (hydrosilylation reaction, $MD_x^{EA}D_yM$)

Experimental Procedure:
In a flask provided with a condenser, 1 g of Preparation 1 is put into solution in 75 mL of dry toluene (13 mg/ml) i.e. a concentration of 78.2 mM of D$^H$ units; 1.2 equivalents of activated ester (Preparation 2) relatively to the number of moles of D$^H$ i.e. 1.97 g of succinimidyl undecenoate (93.8 mM; 26.3 mg/mL) are added.

They are heated to 70° C. and then 2.3 mg of catalyst (Et$_2$S)$_2$PtCl$_2$ (1% relative to the number of moles D$^H$) are added, i.e. a concentration of 0.78 mM (0.03 mg/mL). Heating is stopped after 40 minutes, until total consumption of the Si—H groups (disappearance of the Si—H proton peak in proton NMR at 4.7 ppm and of the peak at 2160 cm$^{-1}$ in FTIR).

The solvent is evaporated under reduced pressure at 77 mbar, 40° C. The polymer is dissolved in 40 mL of acetonitrile. The solution is filtered in an ultrafiltration apparatus (regenerated cellulose membrane) at room temperature.
Characterization:
$^1$H NMR (300 MHz, CDCl$_3$): (δ ppm) δ 0.0 (m, 3H); δ 0.43 (m, 2H); δ 1.20 (m, 12H) δ 1.33 (m, 2H); δ 1.66 (m, 2H); δ 2.52 (m, 2H); δ 2.74 (m, 4H);
$^{13}$C NMR (100 MHz, CDCl$_3$): (δ ppm) δ −4.1, −1.54, 0.1, 16.5, 21.9, 23.6, 24.5, 27.7, 28.1, 28.3, 29.8, 167.6, 168.2.
$^{29}$Si NMR (79.5 MHz, CDCl$_3$): (δ ppm) −21.2 (tm, D$^{EA}$); −22.2 (tm, D) +peak traces at −57 and −65 ppm (T)
SEC DPn 100 (Elution volume in toluene=18 mL)
(DMF (LiBr 0.1%, 60° C.) Elution volume=21.5 mL)
Coupling Reaction of the Functionalized Polymer with the Activated Ester (Preparation 3) with an Aminated Sugar of the Aminopolyol Type 1 g of Preparation 3 is dissolved in 40 ml of DMSO as well as a molar equivalent of D-glucamine relatively to the D$^{EA}$ units i.e. 0.403 g in 40 mL of DMSO, at room temperature. Both solutions are introduced into a reactor with magnetic stirring. They are left under intense stirring. The reaction occurs instantaneously. The polymer is purified by washing with ultrapure water, and then dried in vacuo or else freeze-dried after dispersion in water.
Characterization:
FTIR: 1650-1548 cm$^{-1}$ (NH—CO), 3355 cm$^{-1}$ (OH)
$^1$H NMR (300 MHz, DMSO): (δ ppm) δ 0.0 (m, 3H); δ 0.4 (m, 2H); δ 1.20 (m, 12H) δ 1.43 (m, 2H); δ 2.05 (m, 2H); δ 3-3.7 (m, 10H);
SEC (DMF (LiBr 0.1%, 60° C.) Elution volume=21.3 mL)
DSC: Heating rate 10° C.min$^{-1}$: ascent: T$_g$=13° C.; T$_f$=107° C. (melting temperature); descent: T$_c$=92° C. (crystallization temperature).

EXAMPLE 2

Preparation of poly-(N-glucosamine-undecylamide-methyl)-siloxane containing 100% of Si—N-glucosamine-undecylamide Preparation 4

Grafting of Polymethylhydrosiloxane (Commercial PHMS) with the Activated Ester, Succinimidyl Undecenoate (Preparation 2): (Hydrosilylation Reaction) $MD_x^{EA}M$ Experimental Procedure:

In a flask provided with a condenser, 1 g of PHMS polymer is put into solution in 50 mL of dry toluene (20 mg/ml), i.e. a concentration of 333.3 mM of $D^H$ units; 1.2 equivalents of activated ester (preparation 2) relatively to the number of $D^H$ moles, i.e. 5.62 g of succinimidyl undecenoate (112.4 mg/ml; 400 mM) are added.

They are heated to 70° C. and then 170 μL (0.1% relatively to the number of $D^H$ moles, i.e. a concentration of 0.333 mM of platinum; 3.9 mg/ml of solution) of the platinum catalytic solution (Karstedt's catalyst) in a xylene solution containing 2.2-2.4% of Pt are added. The reaction is stopped after 75 minutes or until total consumption of the Si—H (disappearance of the Si—H proton peak in proton NMR at 4.7 ppm and of the peak at 2160 cm$^{-1}$ in FTIR).

The solvent is evaporated under reduced pressure at 77 mbars, 40° C. The polymer is dissolved in 40 mL of acetonitrile. The solution is filtered in an ultrafiltration apparatus (regenerated cellulose membrane) at room temperature.

Characterization:

$^1$H NMR (300 MHz, CDCl$_3$): (δ ppm) δ 0.0 (m, 3H); δ 0.43 (m, 2H); δ 1.20 (m, 25 12H) δ 1.33 (m, 2H); δ 1.66 (m, 2H); δ 2.52 (m, 2H); δ 2.74 (m, 4H);

$^{13}$C NMR (100 MHz, CDCl$_3$): (δ ppm) δ −4.1, −1.54, 0.1, 16.5, 21.9, 23.6, 24.5, 27.7, 28.1, 28.3, 29.8, 167.6, 168.2.

$^{29}$Si NMR (79.5 MHz, CDCl$_3$): (δ ppm) −21.2 (tm, DEA) +peak traces at −57 and −65 ppm (T)

Coupling Reaction of the Functionalized Polymer with the Activated Ester (Preparation 4) with an Aminated Sugar of the Aminosugar Type 1 g of Preparation 4 is dissolved in 40 ml of DMSO (or DMF) as well as a molar equivalent of free base, glucosamine, relatively to the $D^{EA}$ units, i.e. 2.98 g in 40 mL of DMSO (or DMF), at room temperature. Both solutions are introduced in a reactor with magnetic stirring. They are left with intense stirring. The reaction occurs instantaneously. The polymer is purified by washing with ultrapure water, and is dried in vacuo or else freeze-dried after dispersion in water.

Characterization:

FTIR: 1650-1548 cm-1 (NH—CO), 3355 cm-1 (OH)

1H NMR (300 MHz, DMSO): (δ ppm) δ 0.0 (m, 3H); δ 0.4 (m, 2H); δ 1.20 (m, 12H) δ 1.43 (m, 2H); δ 2.05 (m, 2H); δ 3-3.7 (m, 11H);

The invention claimed is:

1. A polysiloxane grafted with at least one monoaminated saccharide, said monoaminated saccharide(s) being bound by the nitrogen atom of said amine group to a —C=O— group of said polysiloxane in order to form a —C(=O)—NT-, wherein T represents a hydrogen atom or an alkyl or aryl group.

2. The polysiloxane according to claim 1, wherein the polysiloxane has a formula selected from the group consisting of:

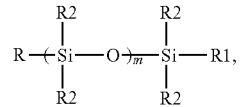

(Ia)

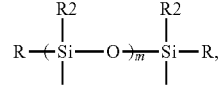

(Ib)

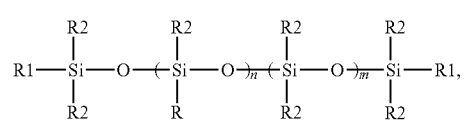

(Ic)

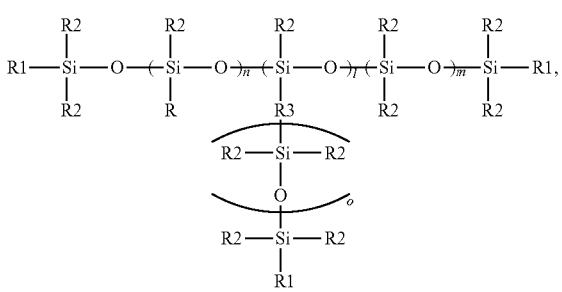

(Id)

and

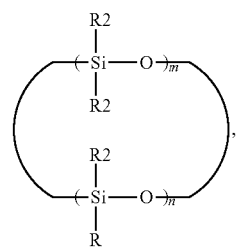

(Ie)

wherein:

each of R1, R2, either identical or different, is a hydrogen atom or a saturated, unsaturated or aromatic, linear, branched or cyclic hydrocarbon group, optionally comprising one or more heteroatoms, and/or one or more halogen atoms and/or epoxide, acrylic groups, C=O, COOU, COU, cyano, NUV, CONUV groups wherein U and V, either identical or different, independently represent a hydrogen atom or an alkyl group;

each of the R groups, being identical or different, is a group of formula —X—C(=O)—NT-Y, wherein X represents an aryl, alkyl, prefluoroalkyl group with 4 to 22 carbon atoms, optionally comprising one or more oxygen atoms, T represents a hydrogen atom or an alkyl or aryl group, Y represents a remainder of a saccharide group, such that Y-NTH represents said monoaminated saccharide, R3 represents a cross-linking bridge that is a saturated, unsaturated or aromatic, linear, branched or cyclic hydrocarbon group, optionally comprising one or more heteroatoms, and/or one or more halogen atoms and/or epoxide, acrylic groups, C=O, COOU, COU, cyano, NUV, CONUV groups wherein U and V, either identical or different, independently represent a hydrogen group or an alkyl group;

n represents an average number strictly greater than 0;

m, l and o, either identical or different, represent average numbers greater than or equal to 0, such that the grafting ratios n/(m+n) or n/(l+m+n+o) is comprised between 1/1000 and 1; and wherein in the formulae (Ia), (Ib), (Ic) (Id) and (Ie) illustrated above, the polysiloxanes may be grafted through one or more saccharide groups randomly or blockwise.

3. The polysiloxane according to claim 1 wherein each of R1 and R2, either identical or different, represents an alkyl, aryl or polyether group.

4. The polysiloxane according to claim 1, wherein m+n or l+m+n+o is less than 10,000.

5. The polysiloxane according to claim 1, wherein X represents an alkyl group with 4 to 22 carbon atoms, optionally comprising one or more oxygen atoms.

6. The polysiloxane according to claim 1, wherein the monoaminated saccharide is selected from mono-, oligo- or poly-saccharides and/or their derivatives, comprising a primary or secondary amine group.

7. The polysiloxane according to claim 1, wherein the saccharide remainder is obtained from one of glucamine, N-methyl-glucamine, glucosamine, galactosamine, mannosamine, and glycosylamines.

8. A method for preparing a grafted polysiloxane according to claim 2 comprising the step for coupling a polysiloxane with at least one activated ester according to one of the formulae (IIa)-(IIe):

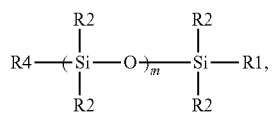
(IIa)

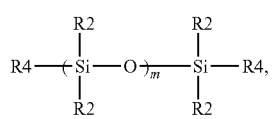
(IIb)

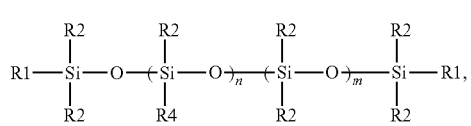
(IIc)

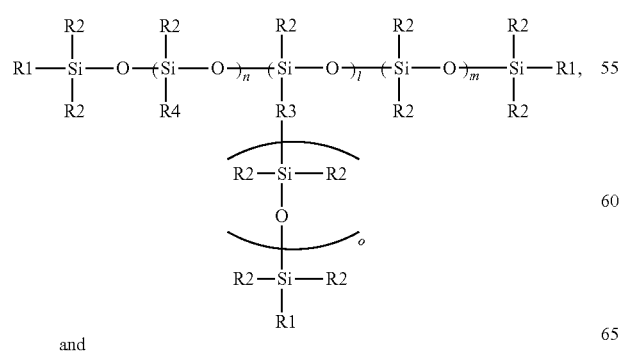
(IId)

and

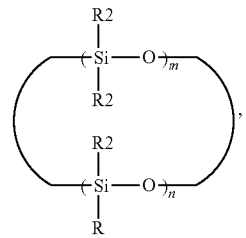
(IIe)

wherein:

R1, R2, R3, n, m, l, o are as previously defined, and each of the R4 groups, either identical or different, is a group of formula —X—C(=O)-A wherein X is as previously defined and A represents an activator group of the carboxylic acid function, with a monoaminated saccharide as previously defined.

9. The method according to claim 8, wherein said monoaminated saccharide is in its basic form.

10. The method according to claim 8, wherein the coupling reaction is carried out without providing any additional base.

11. The method according to claim 8, wherein the coupling reaction is carried out in a solvent allowing comiscibilization of the polysiloxane and of the monoaminated saccharide.

12. The method according to claim 11, wherein the solvent is selected from DMF, DMSO, acetonitrile, THF, dioxane, water or mixtures thereof.

13. The method according to claim 8, wherein A represents an —O-succinimide group wherein the succinimide group may optionally be substituted, or optionally fused with a phenyl group; an —S-alkyl or S-aryl or S-pyridyl group wherein the alkyl, aryl or pyridyl group is optionally substituted with halogen atoms; —O-para-nitrophenyl group and its derivatives; —O-pentafluorophenyl; —O-pentachlorophenyl; —O-benzotriazole and derivatives; —O-benzotriazine and derivatives; -2,2,2-trifluoroethyl; —N-imidazole and derivatives.

14. The method according to claim 8, wherein said polysiloxane functionalized with at least one activated ester (IIa)-(IIe) is prepared by hydrosilylation of a polysiloxane corresponding to formulae (IVa)-(IVe):

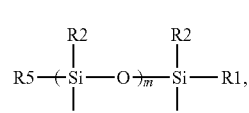
(IVa)

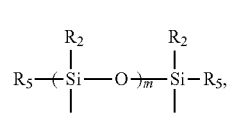
(IVb)

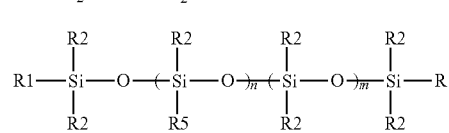
(IVc)

-continued

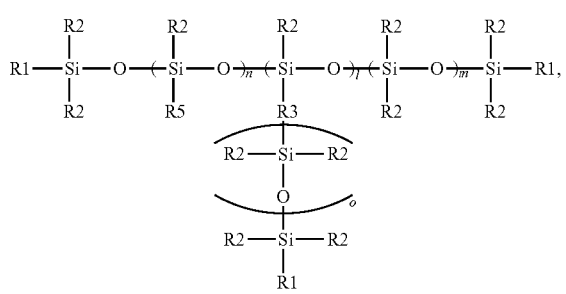  (IVd)

and

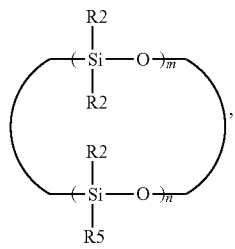  (IVe)

wherein R1, R2, R3 are as previously defined, and R5 represents a hydrogen atom, with an activated ester of formula (III):

$$CHR'=CR''-Z-C(=O)-A \qquad (III)$$

wherein:
R' and R", either identical or different, independently represent a hydrogen atom or an alkyl group,
Z represents an aryl, alkyl group with 2 to 20 carbon atoms, optionally comprising one or more oxygen atoms, and
A is as previously defined, and
wherein —CHR'—CHR"—Z— is equal to X, in the presence of a suitable catalyst.

15. The method according to claim 14, wherein said catalyst is a platinum catalyst.

16. The method according to claim 14, wherein said catalyst is selected from $Pt(Et_2S)_2Cl_2$, $Pt((PhenylCH_2)_2S)_2Cl_2$ and Karstedt's catalyst (platinum/divinyltetramethyldisiloxane complex).

17. The method according to claim 8, further comprising the step for isolating and purifying the obtained polysiloxane.

18. A method of using a polysiloxane according to claim 1 as a surfactant, a surface agent, emulsifier, co-emulsifier, dispersant, co-dispersant, adhesive or component of an adhesive, comprising adding the polysiloxane to a pharmaceutical composition, cosmetic composition or adhesive composition.

19. A pharmaceutical or cosmetic composition comprising a polyxiloxane according to claim 1.

20. A device comprising a polysiloxane according to claim 1.

* * * * *

UNITED STATES PATENT AND TRADEMARK OFFICE
CERTIFICATE OF CORRECTION

PATENT NO. : 8,415,445 B2
APPLICATION NO. : 12/934145
DATED : April 9, 2013
INVENTOR(S) : Juliette Fitremann et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 246 days.

Signed and Sealed this
Fourteenth Day of May, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,415,445 B2  Page 1 of 1
APPLICATION NO. : 12/934145
DATED : April 9, 2013
INVENTOR(S) : Fitremann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 289 days.

Signed and Sealed this
First Day of September, 2015

Michelle K. Lee
*Director of the United States Patent and Trademark Office*